United States Patent
Levin

(10) Patent No.: US 7,303,915 B2
(45) Date of Patent: Dec. 4, 2007

(54) IN VITRO-DIFFERENTIATED RETINAL GANGLION CELLS AND METHOD FOR PRODUCING SAME

(75) Inventor: Leonard A. Levin, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/361,342

(22) Filed: Feb. 24, 2006

(65) Prior Publication Data
US 2006/0189562 A1    Aug. 24, 2006

Related U.S. Application Data

(60) Provisional application No. 60/655,736, filed on Feb. 24, 2005.

(51) Int. Cl.
*C12N 5/00*    (2006.01)
*C12N 5/06*    (2006.01)

(52) U.S. Cl. .................... 435/375; 435/325; 435/353; 435/377

(58) Field of Classification Search .................... None
See application file for complete search history.

(56) References Cited

OTHER PUBLICATIONS

Attwood et al, Amino Acids, Nov. 15, 2006, Epub ahead of print, (pp. 1-12).*
Gray et al, Curr. Med. Chemistry 6: 859-875, 1999.*
Bain et al, Biochem. J 371: 199-204, 2003.*
Sleeper et al, Cell Death and Differentiation 9: 1377-1378, 2002.*
Stein, C.A., Pharmacology and Therapeutics 85: 231-236, 2000.*
Stein, C.A., Sep. J. Clinical Investigation 108(5): 641-644, 2001.*
Caplen, N.J., Gene Therapy 11(16): 1241-1248, 2004.*
Guerin et al, Int. J. Dev. Biol. 50: 665-674, 2006.*
Das et al, Vision Research 45(13): 1653-1666, 2005.*
Adler, R., Development Dynamics 234(3): 454-463, 2006.*
Frassetto et al, Invest. Opthalm. and Visual Sci. 47(1): 427-438, 2006.*
Geiger L, et al., "Reduced redox state allows prolonged survival of axotomized neonatal retinal ganglion cells," Neuroscience 109:635-642 (2002).
Krishnamoorthy R, et al., "Characterization of a transformed rat retinal ganglion cell line," Brain Res. Mol. Brain Res. 86:1-12 (2001).
Moorhouse A, et al., "A patch-clamp investigation of membrane currents in a novel mammalian retinal ganglion cell line," Brain Res. 1003:205-208 (2004).
Page K, et al., "Characterization of a Rac1 signaling pathway to cyclin D(1) expression in airway smooth muscle cells," J. Biol. Chem. 274:22065-22071 (1999).

\* cited by examiner

*Primary Examiner*—Q. Janice Li
*Assistant Examiner*—Kevin K. Hill
(74) *Attorney, Agent, or Firm*—Quarles & Brady LLP

(57) ABSTRACT

In vitro-differentiated retinal ganglion cells can be produced by exposing a mammalian retinal ganglion cell line to a protein kinase inhibitor. The differentiated retinal ganglion cells can be used to identify agents that protect retinal ganglion cells in vivo or in vitro from cell injury (including cell death) and agents that affect retinal ganglion cell ion channel activity.

5 Claims, No Drawings

IN VITRO-DIFFERENTIATED RETINAL GANGLION CELLS AND METHOD FOR PRODUCING SAME

CROSS-REFERENCE TO RELATED APPLICATIONS

This application claims the benefit of U.S. Provisional Patent Application No. 60/655,736, filed Feb. 24, 2005, incorporated herein by reference as if set forth in its entirety.

STATEMENT REGARDING FEDERALLY SPONSORED RESEARCH OR DEVELOPMENT

This invention was made with United States government support awarded by the following agency: National Eye Institute/NIH, EY012492. The United States government has certain rights in this invention.

BACKGROUND OF THE INVENTION

The invention relates generally to in vitro-differentiated retinal ganglion cells and methods for obtaining the cells, and more particularly to methods for obtaining the cells by exposing a cultured retinal ganglion cell line to a protein kinase inhibitor.

The study of optic neuropathies, e.g. glaucoma, and an involved neuron, the retinal ganglion cell (RGC), has been limited to primary cell culture and in vivo models as it is difficult to use cell culture to study RGC pathophysiology. Levin L A, J. Glaucoma 10:S19-21 (2001). Harvesting retinas and identifying RGCs by retrograde labeling or immunocytochemistry is labor intensive and time-consuming. Leahy K M, et al., Exp. Eye Res. 79:131-140 (2004). In addition, RGC purification using antibodies to cell-surface antigens or anatomical location is a lengthy and frequently low-yield process that results in a heterogeneous cell population. Barres B A, et al., Neuron 1:791-803 (1988); Lindqvist N. et al., Brain Res. Mol. Brain Res. Protoc. 10:75-83 (2002). Furthermore, the cells that arise upon differentiation of neuronal cell lines, e.g. pheochromocytoma-derived PC-12 cells, teratoma-derived NT2-N cells or neuroblastoma-derived SY5Y cells, are not retina-derived and do not share phenotypic properties of RGCs. See Greene L A & Tischler A S, Proc. Natl. Acad. Sci. USA 73:2424-2428 (1976); Pleasure S J, et al., J. Neurosci. 12:1802-1815 (1992); and Biedler J L, et al., Cancer Res. 33:2643-2652 (1973).

RGC-5 (ATCC No. PTA 6600), a retinal ganglion cell line derived by transforming postnatal day one rat retinal cells with $\psi_2$ EIA virus, expresses neuronal markers characteristic of RGCs, e.g. Thy-1, Brn-3c, neuritin, and the NMDA-R1 and GABA-B receptors, but does not express glial fibrillary acidic protein (GFAP), an astrocyte marker. Krishnamoorthy R R, et al., Brain Res. Mol. Brain Res. 86:1-12 (2001), incorporated herein by reference as if set forth in its entirety.

Although RGC-5 cells share antigens with RGCs, RGC-5 cells are significantly different, most significantly in that RGC-5 cells are mitotically active while RGCs are not. Also, cultured RGC-5 cells are morphologically more similar to glial cells than to primary RGCs and do not express the repertoire of ion channels that are characteristic of RGCs. Moorhouse A J, et al., Brain Res. 1003;205-208 (2004). As such, what is needed is an RGC-like cell line having pharmacological, biochemical and electrophysiological characteristics that resembles true RGCs more closely than cell lines such as RGC-5 cells.

SUMMARY

The invention is summarized in that an RGC cell line can be treated with a protein kinase inhibitor to yield differentiated cells having characteristics of mammalian-derived primary cultured RGCs that are not observed in the cell line before treatment. The differentiated cells are a suitable alternative to primary RGC cultures and RGC cell lines for RGC-related research and drug development.

In a first aspect, the invention relates to in vitro-differentiated cells having characteristics of primary cultured RGCs that are not observed in an existing cell line derived from primary RGCs. The characteristic properties of the differentiated cells include at least one of (1) a cell division rate substantially lower than that of an available RGC cell line, (2) a number of neurites per cell higher, on average, than that of an available RGC cell line, and (3) of ion channel expression higher than that of an available RGC cell line. Optionally, the differentiated cells also exhibit upregulated expression of a neuronal marker, such as Thy-1 or NMDA-R1, relative to expression by an available RGC cell line.

In a second aspect, the invention relates to a method for producing the in vitro-differentiated cells, which includes the step of exposing an RGC cell line to a protein kinase inhibitor in an amount sufficient to induce cellular differentiation that confers upon the treated cells at least one of (1) a cell division rate substantially lower than that of the RGC cell line, (2) a number of neurites per cell higher, on average, than that of the RGC cell line, and (3) ion channel expression higher than that of the RGC cell line. Optionally, the differentiated cells also exhibit upregulated expression of a neuronal marker, such as Thy-1 or NMDA-R1, relative to expression by the RGC cell line.

In some embodiments, the protein kinase inhibitor is a nonspecific protein kinase inhibitor, a Rho kinase inhibitor or a protein kinase A inhibitor. In other embodiments, the protein kinase inhibitor is staurosporine, H-1152 or H-89.

In some embodiments, the differentiated cells exhibit at least two of the three characteristic features, which two features can be the lower division rate and the higher average number of neurites per cell. In other embodiments, the differentiated cells exhibit three or four of the characteristic features.

In some embodiments, a suitable RGC cell line treated in the method is RGC-5.

In a third aspect, the invention relates to a method for identifying an agent that protects RGCs in vitro or in vivo from an injury (including cell death), the method including the steps of exposing in vitro-differentiated retinal ganglion cells to a candidate agent; inducing a cell injury in the differentiated cells and in control differentiated retinal ganglion cells not exposed to the candidate agent; comparing an extent of injury to the differentiated cells and to the control cells; and identifying an agent that induces less injury in the differentiated cells than in the control cells as an agent that can protect the retinal ganglion cells. In this method, cell injury can be induced before, while, or after the differentiated cells are exposed to a candidate agent.

In a fourth aspect, the invention relates to a method of identifying an agent that affects RGC ion channel activity in vitro or in vivo, the method including the steps of comparing an ion channel activity in in vitro-differentiated RGCs exposed to a candidate agent and in in vitro-differentiated control RGCs not exposed to the candidate agent; and identifying an agent that affects the ion channel activity in the test RGCs relative to the control RGCs.

The in vitro-differentiated RGCs are easily and quickly produced and do not have the problems of batch to batch variation and cell-type impurity encountered with primarily cultured RGCs. The differentiated RGCs can be used for high-throughput screening for agents which are neuroprotective or affect ion channels. The in vitro-differentiated RGC cells can be used without purification by cell-surface markers or anatomical location for biochemical and other assays.

These and other features, aspects and advantages of the present invention will become better understood from the description that follows. The description of preferred embodiments is not intended to limit the invention to cover all modifications, equivalents and alternatives. Reference should therefore be made to the claims to interpret the scope of the invention.

BRIEF DESCRIPTION OF THE DRAWINGS

Not applicable.

DESCRIPTION OF PREFERRED EMBODIMENTS

Cells having terminally differentiated features of primary cultured RGCs can be obtained from an RGC cell line by exposing the cell line to one or more protein kinase inhibitors. In comparison to cells of an RGC cell line, the in vitro-differentiated cells have at least one of the aforementioned characteristic features of primary RGCs not exhibited by an available RGC cell line. Optionally, the differentiated RGCs also have upregulated expression of at least one RGC marker such as Thy-1 or NMDA-R1.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

As used herein, a "cell division rate substantially lower than that of an available RGC cell line" means that the cell proliferation rate of the protein kinase inhibitor-treated cells of an RGC cell line is reduced to about 20% or less of that of non-treated control cells of the same cell line. Preferably, the cell proliferation rate of the protein kinase inhibitor-treated cells is reduced to about 10% or less, about 5% or less, about 3% or less, or about 1% or less of that of the non-treated control cells. The cells treated with the protein kinase inhibitor can completely lose their ability to divide. A skilled artisan is familiar with many methods by which cell proliferation can be assessed. Thymidine or BrdU incorporation during S phase is an example. With thymidine or BrdU incorporation, the ability to divide can be measured by the percentage of cells that incorporate thymidine or BrdU.

As used herein, "neurites" means projections of RGCs that are equal to or greater in length than the cell soma. An increase in the number of neurites can be assessed by comparing the average number of neurites per cell for the protein kinase inhibitor-treated cells of an RGC cell line to that of non-treated control cells of the same cell line. In a preferred embodiment, the protein kinase inhibitor-treated cells have, on average, at least one or two more neurites than the non-treated control cells. For any given RGC line, the average number of neurites per cell is expected to be lower than one. Therefore, any protein kinase inhibitor-treated cells that have on average one, two, or more neurites per cell are considered differentiated cells.

"Increased ion channel expression" refers to expression in the in vitro-differentiated RGCs of any measurable ion channel, such as but not limited to a voltage-gated ion channel, relative to expression of that channel in the cell line. Increased expression can be quantified by evaluating the concentration of mRNA or channel proteins, or by assessing functional activity of the channel. Evaluation at the protein or channel activity levels are preferable.

An RGC cell line obtained from a mammalian animal such as a human, non-human primate, rat, mouse, rabbit, cat, or pig can be treated in vitro to produce the differentiated cells of the invention. A skilled artisan can produce a suitable mammalian RGC cell line using only mature technology available in the art. For example, a mixed retinal cell culture of a mammalian species can be transformed with a virus and an immortalized clone with RGC characteristics can then be characterized and selected as described in Krishnamoorthy et al., supra. In Krishnamoorthy et al., postnatal day one rat retinal cells were transformed with the $\psi_2$ E1A virus, and a clone of cells with RGC characteristics was obtained and used to establish rat RGC cell line RGC-5. RGC-5 was deposited with American Type Culture Collection on Feb. 23, 2005, under ATCC accession number PTA-6600. An available RGC cell line, such as RGC-5, or a newly created RGC cell line can be treated to produce the differentiated cells of the invention.

Both nonspecific protein kinase inhibitors and specific protein kinase inhibitors, or a combination thereof, can be employed in an amount sufficient to induce differentiation of the mammalian RGC cell line. As used herein, "in an amount sufficient to" means an amount sufficient to produce at least one of the three aforementioned features of primary RGCs. Generally, a nonspecific protein kinase inhibitor such as staurosporine is employed. For RGC-5 cells, staurosporine is a strong differentiation inducer and Rho-kinase inhibitor H-1152 and protein kinase A inhibitor H-89 are weak differentiation inducers. Several other protein kinase inhibitors tested alone or in combination in the example below, did not elicit any detectable differentiation response in RGC-5 cells. Therefore, while it is expected that nonspecific protein kinase inhibitors will work in all mammalian RGC lines, the differentiation activity of specific protein kinase inhibitors or a combination thereof depends on individual mammalian RGC cell lines. The details on the differentiation activity of various specific protein kinase inhibitors can be readily determined by a skilled artisan through routine experimentation such as that performed in the example below. In this regard, it is expected that inhibitors of Rho-kinase, protein kinase A, P21-associated kinases, double stranded RNA-dependent protein kinase or any kinase that acts upstream or downstream of any of the foregoing kinases will have differentiation activity in at least some immortalized RGC cell lines.

The ability of RGC-5 cells to remain differentiated following removal of the protein kinase inhibitor(s) can depend upon the lot of fetal bovine serum (FBS) used. Some lots of FBS maintained the cells in a differentiated state, whereas others did not. Consequently, the protein kinase inhibitor(s) should be maintained in the culture media to ensure differentiation. Alternatively, each lot of FBS should be tested for its ability to maintain differentiated cells following the differentiation treatment.

In trials in which a neuroprotective effect of a candidate agent is evaluated, RGC cell death can be induced in many different ways and any can be employed to practice the present invention. One way to induce cell death is by axotomy. Geiger L K, et all, Neuroscience 109:635-642 (2002), incorporated herein by reference as if set forth in its entirety. Another way to induce cell death is by serum/trophic factor deprivation or glutamate toxicity. Krishnamoorthy et al., supra. Other ways to induce cell death include neurite damage, elevated hydrostatic pressure, substrate deprivation, hypoxia, mitochondria depolarization or induction of apoptosis with suitable chemicals.

In trials in which a protective effect of a candidate agent on cell injury or death is evaluated, cell injury rate can be assessed with any of the known methods familiar to a skilled artisan. For cells that are induced to undergo apoptosis, the percentage of apoptotic cells can be measured to determine the death rate. Cell injury can be induced in many different ways, and any of them can be employed to practice the present invention. For example, any method of inducing cell death, supra, can be used to induce cell injury at a non-lethal dose. If a lethal dose is used, the extent of cell injury can be measured at a time point before cell death. Examples of end points that can be used to determine cell injury include retraction of neurites, increased permeability of cytoplasmic or mitochondrial membranes, mitochondrial depolarization, caspase activation, or other cell injury markers that are known to a skilled artisan.

An effect of a candidate agent on ion channel activity can be measured in many different ways and any of them can be used to practice the present invention. As used herein, "expression of one or more channels" means a display of channel activity of an ion channel of interest. Ion channel expression can be measured and assessed by membrane currents, membrane potentials, cellular concentrations of various ions transported by the ion channels of interest, or other suitable parameters with which a skilled artisan is familiar.

Batteries of agents useful for screening candidate agents are commercially available in the form of various chemical libraries. Examples of such libraries include those from ASINEX (e.g., the Combined Wisdom Library of 24,000 manually synthesized organic molecules) and from CHEMBRIDGE CORPORATION (e.g., the DIVERSet™ library of 50,000 manually synthesized chemical compounds; the SCREEN-Set™ library of 24,000 manually synthesized chemical compounds; the CNS-Set™ library of 11,000 compounds; the Cherry-Pick™ library of up to 300,000 compounds). Once an agent having desired activity is identified, further iterations of the screen using one or more libraries of derivatives of that agent can be conducted to identify agents having superior effects.

The invention will be more fully understood upon consideration of the following non-limiting example.

EXAMPLE

This example demonstrates that staurosporine can induce RGC-5 cell differentiation. The differentiated RGC-5 cells express numerous neuronal properties, including but not limited to, halting of proliferation without inducing apoptosis, display of multiple neurites and display of outward rectification typical of most voltage-gated potassium channels and some voltage-gated chloride channels.

Materials and Methods

Materials: Protein kinase inhibitors included: Minocycline (Fisher Scientific; Fair Lawn, N.J.); ZVAD-fmk (Calbiochem; San Diego, Calif.); Thapsigargin (Sigma-Aldrich; St. Louis, Mo.); ionomycin (Sigma-Aldrich); rotenone (Sigma-Aldrich); 3-(4,5-Dimethyl sulfoxide (DMSO; Sigma-Aldrich); Roscovitine (LC Labs; Woburn, Mass.); tyrphostin AG490 (LC Labs); tyrphostin AG1295 (LC Labs); tyrphostin AG1478 (LC Labs); H-89 (LC Labs): HA-1077 (LC Labs); bisindolylmaleimide IX methylsulfate (LC Labs); and staurosporine (SS, from *Streptomyces staurosporeus;* $\geq$98% purity; Alexis Biochemicals; San Diego, Calif.). Cell culture reagents, unless noted, were obtained from BioWhittaker (Rockland, Me.). All labeled antibodies and fluorescent dyes were obtained from Molecular Probes (Eugene, Oreg.).

Cell culture: RGC-5 cells were cultured in Dulbecco's modification of Eagle's medium (DMEM; Mediatech, Inc.; Herndon, Calif.) containing 1 mg/L glucose with L-glutamine, supplemented with 10% FBS, 100 U/ml penicillin and 100 µg/ml streptomycin. Cells were incubated at 37° C. in humidified 5% $CO_2$.

Pharmacological agents were used to induce or to inhibit various signaling pathways within RGC-5 cells. Cells were replated on 12 mm round cover glass in 24 well plates 24 hours prior to pharmacological treatment. Drugs were added for varying lengths of time and then processed for immunocytochemistry.

Immunocytochemistry: Differentiated RGC-5 cells plated on coverslips were fixed with 4% paraformaldehyde (Fisher) in PBS, pH 7.2 for 20 minutes at room temperature, rapidly rinsed with Tris-buffered saline (TBS; 100 mM Tris, pH 7.6, 0.9% NaCl) 3 times for a few seconds each and 2 times for 5 minutes each, and blocked with 5% normal goat serum (BioWhittaker) in TBS for 30 minutes at room temperature. The NMDA-R1 receptor was detected by incubating with purified mouse monoclonal anti-NMDA-R1 antibody (BD Biosciences; San Jose, Calif.; clone 54.1) at 2.5 µg/ml overnight at room temperature, followed by Alexa Fluor™ 594 goat anti-mouse IgG at 10 µg/ml in blocking buffer at room temperature for 90 minutes. Alexa Fluor™ 594 fluorescence was detected with a Texas Red filter set (excitation 560±20 nm, dichroic 595 nm long-pass, emission 630±30 nm). Thy-1 was detected after fixing and blocking by incubating with rabbit anti-Thy-1 polyclonal IgG (Santa Cruz Biotechnology; Santa Cruz, Calif.) at 20 µg/ml overnight at 4° C., followed by Alexa Fluor 488 goat anti-rabbit IgG at 4 µg/ml at room temperature for 60 minutes. Alexa Fluor 488 fluorescence was detected with a FITC filter set (excitation 470±20 nm, dichroic 505 nm long-pass, emission 540±20 nm) filter set. Nuclear condensation changes characteristic of apoptosis were assessed by adding Hoechst 33258 dye (Molecular Probes) at 10 µg/ml for the final 30 minutes of pharmacological treatment prior to cell fixation, and viewed with a DAPI filter set (excitation 540±12.5 nm, dichroic 565 m-n, emission 630±30 nm). Cover slips were then transferred and mounted on microscope slides with Gel/Mount (Biomeda Corporation; Foster City, Calif.). Slides were viewed with a Zeiss Axiophot upright microscope with Nomarski optics and epifluorescence, and images acquired with Zeiss Axiovision software at 1300×1030 resolution.

Immunoblot analysis: Rat RGC-5 cells were grown to approximately 70% confluency on 100 mm tissue culture plates (BD Biosciences; Bedford, Mass.) and either treated with staurosporine to a final concentration of 316 nM for 3 days or harvested without treatment. Cells were lysed in PBS containing 1% Igepal CA-630, 0.5% sodium deoxycholate, 0.1% sodium dodecyl sulfate (Fisher Scientific), 0.10 mg/ml phenylmethylsulfonyl fluoride (Sigma), and Complete mini Protease Inhibitor Cocktail Tablet (5 mg/ml; Roche Diagnostics; Mannheim, Germany) for 15 minutes at 4° C., then scraped off the plate and collected. Cell lysates from two tissue culture plates were pooled for each sample and incubated on ice for sixty minutes. After centrifugation at 10,000 g for 10 minutes at 4° C., the pellets were sonicated on ice for two 15 seconds bursts and centrifuged again at 10,000 g for 10 minutes.

The protein concentrations of the supernatants were determined by Bradford assay, and 1 mg of total protein from differentiated and undifferentiated cells was boiled in the presence of 4× lithium dodecyl sulfate (LDS) sample buffer (Invitrogen; Carlsbad, Calif.) plus 5% β-mercaptoethanol, resolved on a NuPAGE Bis-Tris 4-12% polyacrylamide gel (Invitrogen), and transferred overnight at 50 mA to nitrocellulose membrane in a Bio-Rad Mini Protean II transfer apparatus (BioRad Laboratories; Hercules, Calif.).

After transfer, the membrane was blocked with 5% non-fat milk in TBS (pH 8.0) for 30-60 minutes, and then probed with primary antibodies to RGC marker proteins in blocking buffer. Antibodies used included purified rabbit polyclonal anti-microtubule-associated protein 2 (1:2000; Chemicon; Temecula, Calif.), polyclonal rabbit anti-Thy-1 (1:100; Santa Cruz Biotechnology), and polyclonal rabbit anti-actin (1:1000; Sigma). Blots were rinsed 3 times with TBS containing 0.05% Tween-20 (Fisher Scientific), then washed 5 times for 10 minutes each at room temperature on an orbital shaker. Secondary antibodies used were purified HRP-conjugated goat anti-rabbit IgG and purified HRP-conjugated goat anti-mouse IgG (1:5000; Jackson Immunoresearch Laboratories; West Grove, Pa.), and were incubated for 1 hour at room temperature, followed by 3 rinses and five 10 minute washes with TBS containing Tween-20 at room temperature on an orbital shaker. Blots were treated with freshly prepared ECL solution containing 100 mM Tris HCl pH 8.5, 1.25 mM luminol, 225 μM p-coumaric acid (Sigma), and 1 mM $H_2O_2$ (Fisher Scientific) for 1 minute, and excess solution was allowed to drip off. The blots were then exposed to Kodak BioMax XAR film (Eastman Kodak Company; Rochester, N.Y.) and developed. The films were scanned at 1600 dpi and band density was determined by comparing total intensity in an area containing the band of interest to the intensity of an equal size area of background using NIH ImageJ software. Band density readings are presented with respect to the density of the band from the control, untreated cell condition.

Cell morphology: Photomicrographs were taken at 400× total magnification with Nomarski optics, digitized as above, and stored as JPEG images. The pictures were then batch analyzed off-line to assess the development of neurites. A total of fifty cells from each condition were analyzed. The fifty cells assessed for neurite outgrowth in each condition were selected to include all cells in each photomicrograph for which the neurite tree was visible, and continuing with a new photomicrograph until fifty cells were analyzed. Projections from the cell were classified as neurites if they were equal or greater in length than the cell soma. Only branches arising from the soma were counted. The neurite counts were expressed as mean±S.E.M.

Cell proliferation: Cells were incubated with 100 μM bromodeoxyuridine (BrdU; Sigma-Aldrich) at 37° C. for 2 hours. Media was aspirated and cells immediately fixed with ice-cold glycine-ethanol (150 mM glycine, 70% EtOH, pH 2.0) for 30 minutes at −20° C. Wells were washed with TBS, incubated with blocking buffer (0.3% Triton X-100, 5% normal goat serum in TBS) for 30 minutes at room temperature, then incubated overnight at 4° C. with monoclonal mouse anti-BrdU (Sigma-Aldrich; clone Bu 33) at 4 μg/ml in blocking buffer. After washing, cells were incubated for 1 hour at room temperature with Alexa Fluor 594 goat anti-mouse IgG (2 μg/ml) in TBS. Proliferating cells were identified by superimposing BrdU fluorescence and Nomarski microscopy images of the same fields.

Cell number: Cells were plated in 96 well plates and 3-(4,5-dimethylthiazol-2-yl)-2,5-diphenyltetrazolium bromide (MTT) added immediately to a final concentration of 500 μg/ml. Plates were incubated for 5 hours at 37° C. The media was then replaced with 200 μl of DMSO, which was pipetted up and down to dissolve the formazan crystals, and the plate incubated at 37° C. for 5 minutes. Absorbance was measured at 550 nm on a THERMOmax™ microplate reader (Molecular Devices; Sunnyvale, Calif.). All readings were normalized to a standard curve derived from known numbers of cells.

Electrophysiology: Whole-cell voltage-clamp recordings were made at room temperature using borosilicate glass pipettes (3-6 MΩ resistance) filled with (in mM): 140 KCl, 10 EGTA, 2 MgATP, 20 phosphocreatine and 10 HEPES, pH 7.3, 315 mOsm. The extracellular solution contained (in mM) 145 NaCl, 2.5 KCl, 2 $CaCl_2$, 1 $MgCl_2$, 10 HEPES, 4 glucose, pH 7.4, 325 mOsm. Series resistance was monitored during recordings (5.4±0.65 MΩ, mean±SEM, n=17 acceptable recordings). No series resistance compensation was used. Currents were low-pass filtered at 1-5 kHz with a four-pole Bessel filter, and digitized at a rate no less than twice the filter frequency. Data were collected using an Axopatch 200B amplifier and Digidata 1320A digitizer, controlled by AxoGraph software (Axon Instruments Inc.; Foster City, Calif.) running on a Macintosh G4 (Apple Computer Inc.; Cupertino, Calif.). Analysis and curve fitting was also performed using AxoGraph.

Voltage-gated currents were studied by applying 10 ms voltage steps from −100 to +90 mV in 10 mV increments, from a holding potential of −60 mV. This protocol was run 2-6 times on each cell and the currents evoked at each potential were averaged. Passive leak and capacitive currents were removed by scaling the average current evoked at −70 mV, and subtracting the result from the average current obtained at each voltage. Current amplitudes were measured at steady-state (i.e., near the end of the voltage step), and the slope conductance was computed as the difference between successive amplitudes, divided by the 10 mV step increment.

Analysis of kinase phosphorylation targets: Total cell lysates were prepared as described in Zhang H, et al., J Biol Chem 276:6905-6908 (2001). Cells were washed with ice-cold PBS, scraped, and centrifuged at 3,200 g for five minutes. The pellets were resuspended in lysis buffer (Kinexus Bioinformatics; Vancouver, BC, Canada) supplemented with 5 mM pepstatin A (Roche; Indianapolis, Ind.), and Complete mini protease inhibitor cocktail (Roche). The suspensions were sonicated on ice for two 15-second bursts, followed by centrifugation at 100,000 g for 30 minutes at 4° C. The protein concentrations of the supernatants were determined by Bradford assay and 500 μg protein from undifferentiated and differentiated cells resolved on 13% single lane SDS polyacrylamide gels. Bradford M M, Anal Biochem 72:248-254 (1976). These were then transferred to nitrocellulose membranes. Using a twenty-lane multiblotter (BioRad; Hercules, Calif.), the membranes were incubated with different mixtures of up to three antibodies per lane that react with a distinct subset of at least thirty-seven known phosphorylated sites of cell signaling proteins of distinct molecular masses. After further incubation with a mixture of relevant HRP conjugated secondary antibodies (Santa Cruz Biotechnology), the blots were developed using ECL Plus reagent (Amersham Pharmacia; Piscataway, N.J.) and signals quantified using Quantity One software (BioRad). The panel of target phosphoproteins detected by the Kinetworks™ KPSS 2.1 screen are listed in Table 1. Detailed information and protocols of the Kinetworks™ analysis can be found at the Kinexus Bioinformatics Corporations website.

TABLE 1

Phosphorylation Sites Detected in Kinexus KPSS 2.1 Screen c-Kit (Y703)
c-Kit (Y730)
c-Kit (Y936)
c-Met Receptor Tyrosine Kinase (Y1003)
c-Met Receptor Tyrosine Kinase (Y1230/Y1234/Y1235)
Cyclin-dependent kinase 1 (T14/Y15)
Epidermal Growth Factor Receptor (Y1068)
Epidermal Growth Factor Receptor (Y1148)
ErbB2 receptor tyrosine kinase (Y1139)
Eukaryotic Translation Initiation Factor 2B epsilon subunit (S539)
Extracellular signal-regulated kinase 1 (T202/Y204)
Extracellular signal-regulated kinase 2 (T185/Y187)
Focal Adhesion Kinase (S722)
Focal Adhesion Kinase (S910)
Focal Adhesion Kinase (Y576)
Focal Adhesion Kinase (Y577)
Insulin Receptor (Y972)
Insulin Receptor Substrate-1 (Y1179)
Insulin Receptor Substrate-1 (Y612)
Insulin/Insulin-Like Growth Factor-1 Receptor (Y1162/Y1163)
Lck (S158)
Lck (Y192)
Lck (Y505)
MAP Kinase Kinase 1 (S298)
MAP Kinase Kinase 1 (T292)
MAP Kinase Kinase 1 (T386)
MAP Kinase Kinase 2 (T394) (murine)
Oncogene SRC (Y418)
Oncogene SRC (Y529)
p38 alpha MAP kinase T180/Y182
Protein kinase B alpha (Akt1) (S473)
Protein kinase R (T451)
Retinoblastoma protein (S612)
SH2 domain-containing transforming protein 1 (Y239/Y240)(52)
SH2 domain-containing transforming protein 1 (Y239/Y240)(66)
SH2 domain-containing transforming protein 1 (Y239/Y240)(46)
Stress-activated protein kinase (JNK) (T183/Y185) (39)
Stress-activated protein kinase (JNK) (T183/Y185) (47)
Tumor suppressor p53 (S392)

Results

Staurosporine induces morphological differentiation of RGC-5 cells: Treatment with amounts of staurosporine ranging from 316 nM to 1.78 µM for twenty-four hours induced a significant dose-dependent formation of neurites and changed the soma from flat and polygonal to rounded and moderately elevated, consistent with a neuronal morphology. The change in morphology was quantified by counting neurites, defined as cell projections greater than the length of the soma. When RGC-5 cells were treated with staurosporine ranging from 100 nM to 3.16 µM a dramatic increase in neurite count was observed after treatment. The number of neurites in each condition is expressed as average±SEM from 50 cells. Cells treated with vehicle control had 0.16±0.05 neurites per cell, while cells treated with 1 µM staurosporine had 2.94±0.11 neurites per cell. Neurites were multiply branched. Staurosporine concentrations higher than 1.78 µM were frequently toxic, as evidenced by a necrotic appearance of the cell body and blebbing and disruption of the neurite tree. Serum-deprivation did not induce neurite expression in RGC-5 cells (0.22±0.06 vs. 0.16±0.05 in control; p=0.45).

Previous experiments showed that after twenty-four hours of exposure to SS, RGC-5 cells had differentiated. We tested the length of staurosporine exposure required to induce differentiation of the RGC-5 cells after staurosporine was removed from the cell culture media. Cells were treated with 1 µM SS. At zero, ten, thirty seconds and one, five, ten, thirty and sixty minutes, the media was aspirated the wells rinsed once with fresh pre-warmed media, and incubated in fresh media for twenty-four hours from the time of treatment. Cells treated for as little as sixty seconds had definite morphological signs of differentiation. Cells had increasingly well-developed branching projections as staurosporine exposure time was lengthened.

Neurite branching patterns of differentiated RGC-5 cells were examined and the number of branches counted. Neurite branching, average neurite length, and total neurite length was negligible in untreated cells. Differentiation induced by exposure to 316 nM staurosporine led to minimally branched neurites, whereas higher concentrations induced more branching. In addition to increased branching, a moderate (1 µM) concentration of staurosporine promoted longer average and total neurite outgrowth. At high (3.16 µM) staurosporine concentrations the neurite branching was greater, but the average and total process length decreased somewhat. All comparisons between differentiated and undifferentiated RGC-5 cells of neurite number, branches, average neurite length and total length were significant at $p<0.05$, for each concentration of SS.

Staurosporine switches RGC-5 cells into a post-mitotic state without affecting viability: RGC-5 cells are mitotically active. To test whether staurosporine induced terminal differentiation, we measured incorporation of thymidine analog BrdU during S phase in SS-treated and control cells. RGC-5 cells were incubated with 100 µM BrdU for the final 2 hours of a 24-hour incubation with 1 µM SS, followed by anti-BrdU immunofluorescence staining (red fluorescence overlapped with Nomarski images). Staurosporine (1 µM for twenty-four hours) caused cells to become BrdU$^-$, i.e. post-mitotic. BrdU incorporation was seen in 69.5% of untreated control cells, compared to 2.2% of SS-treated cells, consistent with a switch to a non-proliferating state.

SS is commonly used to initiate apoptosis, and the lack of BrdU incorporation could be due to cell death and not to the transition to a post-mitotic phenotype. To explore this possibility, we used the MTT assay in differentiated and undifferentiated RGC-5 cells. The MTT assay is a quantitative colorimetric method to for measuring cell proliferation and viability. Cell numbers after staurosporine treatment increased slightly in number over a twenty-four hour period (7133±266 cells at 1 hour after culture vs. 10,094±1023 cells at twenty-four hours; p=0.012), while untreated cells predictably increased dramatically (7,666±471 cells at 1 hour vs. 16,579±653 at 24 hours; p<0.000001). Given the lack of BrdU incorporation in SS-treated cells, the small increase in MTT metabolisms indicates that differentiated cells have moderately increased redox activity. Marshall N J, et al., Growth Regul. 5:69-84 (1995).

Differentiated RGC-5 cells retain expression of retinal ganglion cell markers: RGC-5 cells express NMDA-R1 and Thy-1, which are both seen in mature RGCs (Krishnamoorthy et al., supra). NMDA-R1 and Thy-1 labeling was seen in both undifferentiated and differentiated RGC-5 cells with visibly more intense staining in the latter. Untreated or SS-differentiated RGC-5 cells were incubated for twenty-four hours then stained with using mouse anti-glutamate receptor (anti-NMDA-R1; clone 54.1) followed by Alexa Fluor™ 594 goat anti-mouse IgG, or with rabbit anti-Thy-1 polyclonal IgG followed by Alexa Fluor 488 goat anti-rabbit IgG.

To quantify the comparative levels of ganglion cell marker expression, protein samples prepared from RGC-5 cells differentiated for three days in the presence of 316 nM staurosporine were analyzed by immunoblotting. Western blot analysis revealed increased levels of Thy-1 and the dendritic marker microtubule-associated protein 2 (MAP-2), a dendritic marker, after differentiation.

Staurosporine treatment induces expression of voltage-gated ion channels: To determine whether the differentiating effects of staurosporine treatment also involved changes in the electrophysiological properties of RGC-5 cells, membrane currents were assessed using whole-cell voltage-clamp recording. Untreated cells had an input resistance of 55±10 MΩ (mean±SEM), an apparent capacitance of 28±2 pF, and a resting potential of −34±0.5 mV (n=4). After subtracting passive components, a small residual outward current was present at depolarized potentials, yielding a maximal conductance of 3.1±0.5 nS at +90 mV. Three staurosporine treatment protocols were tested (given as hours in staurosporine with duration of the following incubation in medium alone in brackets): 1 hr [24 hr], 1 hr [48 hr], and 22 hr [2 hr]. Staurosporine induced some changes in passive properties, as judged by ANOVA and Dunnett's post hoc test. After treatment, input resistances were 397±171 MΩ (1 hr [24 hr], n=5, not significant, n.s.), 322±89 MΩ (1 hr [48 hr], n=4, n.s.), and 843±201 (22 hr [2 hr]; n=3, $p<0.05$), apparent capacitances were 31±5 pF (1 hr [24 hr], n.s.), 44±3 pF (1 hr [48 hr], $p<0.05$), and 38±3 (22 hr [2 hr]; n.s.), and resting potentials were −27±9 mV (1 hr [24 hr], n=5, n.s.), −9±6 mV (1 hr [48 hr], n.s.), and −11±3 (22 hr [2 hr]; n.s.). The larger capacitance in some cells is consistent with the elaboration of neuronal-like processes. In addition, although not significant by ANOVA, staurosporine induced sizeable increases in voltage-gated conductance in all groups of treated cells. After leak subtraction, outward currents had conductances at +90 mV of 14±5 nS (1 hr [24 hr], n.s.), 7±3 nS (1 hr [48 hr], n.s.), and 5±3 nS (22 hr [2 hr], n.s.).

Inspection of the spread in the data reveals that some treated cells had small conductance similar to untreated cells, whereas others had much larger conductance. This bimodal distribution probably accounts for the inability to detect significant differences. We therefore further examined cells with conductances greater than the mean of the untreated group plus twice its standard deviation. The probability of finding such values should be extremely low if there were truly no differences between groups. However, half of the treated cells had conductances in this range, suggesting that staurosporine induced the expression of voltage-gated current in a large fraction of cells. In these cells, the current increased monotonically as a function of voltage and could be fit with a Boltzmann function in the most robust treatment group (i.e., 1 hr [24 hr]), yielding a maximal conductance of 26 nS and an apparent half-activation voltage of +48 mV. Because treated cells display neuronal-like processes, we cannot be assured of adequate space clamp. Thus, the strongly positive activation range and shallow slope factor we observed may not accurately reflect the biophysical characteristics of the expressed channels. Nonetheless, it seems clear that staurosporine altered the electrical properties of a subset of treated cells.

Staurosporine differentiation is independent of apoptosis induction: staurosporine can induces apoptosis, and its differentiating effect on RGC-5 cells could be a side-effect of apoptotic cell death. We tested this possibility in the following three ways: (1) exposing cells to staurosporine while inhibiting apoptosis; (2) attempting to differentiate cells with other agents that induce apoptosis; and (3) looking for nuclear changes of apoptosis in SS-treated cells.

We differentiated RGC-5 cells with staurosporine in the presence of two apoptosis inhibitors with different mechanisms of action, minocycline (which inhibits cytochrome c release) and ZVAD-fmk (a broad-spectrum caspase inhibitor). Following thirty minutes pretreatment with 10 μM minocycline or 20 μM ZVAD-fmk, RGC-5 cells were washed and then incubated with 1 μM staurosporine for twenty-four hours. Cells pre-treated with minocycline or ZVAD-fmk and subsequently exposed to staurosporine underwent morphological differentiation similar to cells that were not pretreated with apoptosis inhibitors. Minocycline or ZVAD-fmk did not inhibit differentiation with SS. Undifferentiated cells treated with minocycline or ZVAD-fmk alone did not differentiate.

We then induced apoptosis in RGC-5 cells with three different drugs and determined that none induced any differentiating effects. Rotenone (10 μM) was used to inhibit complex I of the mitochondrial electron transport chain, ionomycin (20 μM) to elevate intracellular calcium by acting as an ionophore, and thapsigargin (10 μM) to elevate intracellular calcium by inhibiting endoplasmic reticulum $Ca^{++}$-ATPase. None resulted in morphological evidence of differentiation, although thapsigargin did cause cells to become more spindle-shaped.

Finally, we assessed SS-treated RGC-5 cells for nuclear morphological changes of apoptosis. We observed that apoptosis inducers other than staurosporine did not differentiate RGC-5 cells. After a twenty-four hour incubation with SS, Hoechst 33258 (10 μg/ml) was added for thirty minutes and cells examined. Staurosporine-treated cells were the same as controls, with finely granular nuclei that were not compacted. As expected, ionomycin and rotenone induced nuclear condensation, thapsigargin did not nor did SS.

Differentiation with staurosporine is only partly replicated by more specific kinase inhibitors: staurosporine is a nonspecific kinase inhibitor. To determine which kinase(s) could be responsible for differentiation, we attempted to differentiate RGC-5 cells with different relatively specific kinase inhibitors, alone or in combination, at a wide range of concentrations. Inhibitors were chosen based on published data (Bain J, et al., Biochem J 371:199-204, 2003) demonstrating that staurosporine inhibited the respective kinase. Table 2 profiles the effects of various kinase inhibitors on RGC-5 cells.

None of the kinase inhibitors alone or in combination differentiated RGC-5 cells to the same degree as SS, although two produced observable changes in morphology consistent with partial differentiation. H-1152, which primarily inhibits Rho-kinase (Ki=1.6 nM) and H-89, which primarily inhibits protein kinase A (Ki=50 nM induced mild elevation in neurite counts, but did not produce rounding of the cell soma. Staurosporine-treated (3.16 μM) cells expressed 3.04±0.16 neurites, whereas H-1152-treated (1 μM) and H-89-treated (56.2 μM) RGC-5 cells expressed 1.06±0.15 and 1.80±0.16 neurites, respectively.

Staurosporine rapidly induces changes in phosphorylation targets of several protein kinases: Because of the difficulty in replicating the differentiating effects of staurosporine with a broad array of relatively specific protein kinase inhibitors, we used a kinomic approach, studying the change in phosphorylation status of multiple kinase targets with an immunoblotting methodology. Pelech S, Curr. Pharm. Biotechnol.

5:69-77 (2004). Because we wanted to determine the earliest changes associated with signaling differentiation, and not those associated with its execution, we analyzed cells that had been exposed to 1 µM staurosporine for 5 minutes, a period that committed the cells to differentiation without altering morphology.

Western blotting was used to examine kinase phosphorylation at thirty-nine known sites. Compared to sham-treated cells, there was a 90% increase in the S722 target of focal adhesion kinase (FAK). Other phosphorylation targets with notable differences from control were c-Kit$_{Y703}$ (43% increase), ERK1$_{T202/Y204}$ (not present in control), ERK2$_{T185/Y187}$ (59% decrease), CDK1$_{T14/Y15}$ (64% increase), MEK1$_{S298}$ (100% decrease), and PKR$_{T451}$ (100% decrease). Normalized differences between staurosporine treatment and control revealed several proteins with marked changes in phosphorylation levels.

The present invention is not intended to be limited to the foregoing example, but encompasses all such modifications and variations as come within the scope of the appended claims.

The invention claimed is:

1. A method for obtaining in vitro-differentiated retinal ganglion cells (RGC) from a rat RGC-5 cell line, the method comprising the step of:

exposing cells of the rat RGC-5 cell line to an amount of a known protein kinase inhibitor sufficient to differentiate the cells, wherein the protein kinase inhibitor is selected from staurosporine, H-1152 or H-89, and wherein the differentiated cells exhibit at least one feature selected from (1) a cell division rate substantially lower than that of the RGC-5 cell line, (2) a higher number of neurite per cell, on average, than that of the RGC-5 cell line, or (3) expression of one or more ion channels higher than that of the RGC-5 cell line.

TABLE 2

| Kinase | Roscovitine | Tyrphostin AG490 | Tyrphostin AG1295 | Tyrphostin AG1478 | H-89 | HA-1077 | Bisindolyl-maleimide IX | Kenpaullone | H-1152 | IBMX | PD98059 | LY290042 | SS* |
|---|---|---|---|---|---|---|---|---|---|---|---|---|---|
| CDK1/cyclin B | X | | | | | | | X | | | | | X |
| CDK2/cyclin A | X | | | | | | | X | | | | | X |
| CDK5 | X | | | | | | | X | | | | | X |
| JAK-2 | | X | | | | | | | | | | | X |
| EGFR | | X | | X | | | | | | | | | X |
| PDGFR | | | X | | | | | | | | | | X |
| PKA | | | | | X | | | | | | | | X |
| MLCK | | | | | | X | | | | | | | X |
| CAM | | | | | | X | | | | | | | X |
| PKC | | | | | | | X | | | | | | X |
| Rho-Kinase | | | | | | | | | X | | | | X |
| cAMP PDE | | | | | | | | | | X | | | (via PKC) |
| cGMP PDE | | | | | | | | | | X | | | (via PKC) |
| MEK | | | | | | | | | | | X | | X |
| Akt | | | | | | | | | | | | X | X |

Table 3 summarizes the differences and similarities observed among primary retinal ganglion cells (RGC), the RGC-5 cell line and differentiated cells of the invention.

TABLE 3

| FEATURE | RGC-5 | Differentiated RGC-5 | RGC |
|---|---|---|---|
| Morphology | Flat, polygonal, few neurites | Small soma, several long neurites | Small soma, several long neurites |
| Mitotic State | Proliferating | Non-proliferating | Non-proliferating |
| Ion Channels | Cl$_v$ | Most likely outward rectifying potassium channel | Na$_v$1.1, Na$_v$1.2, Na$_v$1.3, and Na$_v$1.6 |
| | K$_v$ | | Ca$_v$3.1, Ca$_v$3.2, and Ca$_v$3.3 |
| | K$_{ir}$ | | K$_v$ |
| | | | K$_{ir}$1.1, K$_{ir}$2.1, K$_{ir}$2.3, K$_{ir}$3.1, K$_{ir}$3.2, and K$_{ir}$3.3 |
| | | | ASIC1a, ASIC2a, ASIC2b, ASIC3, and ASIC4 |
| Neuronal Markers | Thy-1, NMDA-R1, GABA-B Receptor, Brn-3C, Neuritin, synaptophysin expression | Thy-1, NMDA-R1. (GABA-B Receptor, Brn-3C, Neuritin, synaptophysin expression - not tested) | Thy-1, GFAP, β-Actin, Brn 3-C, NGF, NT-3, NT-4, Neurtin, TrkA, TrkB, P75, CNTF, BDNF, GDNF, GABA-B, Synaptophysin |

2. A method as recited in claim 1, wherein the known protein kinase inhibitor is staurosporine.

3. A method as recited in claim 1, wherein the differentiated cells exhibit at least two of the features.

4. A method as recited in claim 3, wherein the at least two features are the substantially reduced cell division rate and the higher number of neurites per cell.

5. A method as recited in claim 1, wherein the differentiated cells further exhibit upregulated expression of a neuronal marker selected from Thy-1, NMDA-R1, GABA-B receptor, Brn-3C, neuritin, synaptophysin, GFAP, β-Actin, NGF, NT-3, NT-4, TrkA, TrkB, P75, CNTF, BDNF, or GDNF.

* * * * *